US008303592B2

(12) United States Patent
Missos et al.

(10) Patent No.: US 8,303,592 B2
(45) Date of Patent: Nov. 6, 2012

(54) SYSTEM FOR FORMING A TENDON-BONE GRAFT

(75) Inventors: Nicholas B. Missos, Winona Lake, IN (US); Mark V. Vandewalle, Pierceton, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1423 days.

(21) Appl. No.: 11/867,928

(22) Filed: Oct. 5, 2007

(65) Prior Publication Data

US 2009/0093853 A1 Apr. 9, 2009

(51) Int. Cl.
*A61B 17/00* (2006.01)
(52) U.S. Cl. ............................. 606/79; 606/84; 409/303
(58) Field of Classification Search .................. 606/79, 606/84, 167; 623/923; 409/59, 60, 295, 409/303, 310–312, 315, 316, 288, 308, 309, 409/138, 73, 75; 144/117.1, 117.3, 117.4, 144/121, 129, 130, 134.2, 152
See application file for complete search history.

(56) References Cited

U.S. PATENT DOCUMENTS

| 43,909 | A | 8/1864 | Hair |
|---|---|---|---|
| 493,730 | A | 3/1893 | MacKenzie |
| 1,911,873 | A | 5/1933 | Balton |
| 2,573,462 | A | 10/1951 | Lindsey |
| 2,591,516 | A | 4/1952 | Darnell |
| 3,835,849 | A | 9/1974 | McGuire |
| 3,848,601 | A | 11/1974 | Ma et al. |
| 4,007,732 | A | 2/1977 | Kvavle et al. |
| 4,010,737 | A | 3/1977 | Vilaghy et al. |
| 4,059,115 | A | 11/1977 | Jumashev et al. |
| 4,177,797 | A | 12/1979 | Baylis et al. |
| 4,416,278 | A | 11/1983 | Miller |
| 4,565,192 | A | 1/1986 | Shapiro |
| 4,627,853 | A | 12/1986 | Campbell et al. |
| 4,649,918 | A | 3/1987 | Pegg et al. |
| 4,741,651 | A | 5/1988 | Despres |
| 4,782,833 | A | 11/1988 | Einhorn et al. |
| 4,904,259 | A | 2/1990 | Itay |
| 4,913,143 | A | 4/1990 | Oloff et al. |

(Continued)

FOREIGN PATENT DOCUMENTS

DE 19503504 A1 3/1996

(Continued)

OTHER PUBLICATIONS

"Matrices for Cartilage Repair," Coutes, et al., published in Clinical Orthopaedics & Related Research, No. 391S pp. 271-S279, copyright 2001 Lippincott Williams & Wilkins, Inc.

(Continued)

*Primary Examiner* — Kevin T Truong
*Assistant Examiner* — Andrew Yang
(74) *Attorney, Agent, or Firm* — Harness, Dickey (57) ABSTRACT

A system for forming a tendon-bone graft. The system can include at least one support that is adapted to support the tendon-bone graft. The system can further include at least one clamp that is adapted to engage the tendon-bone graft to clamp the tendon-bone graft to the at least one support. The system can also include at least one cutting member that is operable to resect the tendon-bone graft. The at least one cutting member or the at least one support can be moveable relative to the other of the at least one cutting member or the at least one support to resect the tendon-bone graft.

20 Claims, 7 Drawing Sheets

U.S. PATENT DOCUMENTS

| | | | |
|---|---|---|---|
| 4,936,313 | A | 6/1990 | Burkhardt et al. |
| 5,041,117 | A | 8/1991 | Engelhardt |
| 5,053,050 | A | 10/1991 | Itay |
| 5,139,520 | A | 8/1992 | Rosenberg |
| 5,152,763 | A | 10/1992 | Johnson |
| 5,197,967 | A | 3/1993 | Wilson |
| 5,211,647 | A | 5/1993 | Schmieding |
| 5,269,786 | A | 12/1993 | Morgan |
| 5,320,115 | A | 6/1994 | Kenna |
| 5,320,626 | A | 6/1994 | Schmieding |
| 5,341,816 | A | 8/1994 | Allen |
| 5,397,357 | A | 3/1995 | Schmieding et al. |
| 5,415,651 | A | 5/1995 | Schmieding |
| 5,423,823 | A | 6/1995 | Schmieding |
| 5,496,326 | A | 3/1996 | Johnson |
| 5,513,662 | A | 5/1996 | Morse et al. |
| 5,540,692 | A | 7/1996 | Tidwell |
| 5,562,669 | A | 10/1996 | McGuire |
| 5,603,716 | A | 2/1997 | Morgan et al. |
| 5,655,546 | A | 8/1997 | Halpern |
| 5,733,289 | A | 3/1998 | Seedhom et al. |
| 5,782,835 | A | 7/1998 | Hart et al. |
| 5,785,714 | A | 7/1998 | Morgan et al. |
| 5,817,098 | A | 10/1998 | Albrektsson et al. |
| 5,827,288 | A | 10/1998 | Umber et al. |
| 5,865,834 | A | 2/1999 | McGuire |
| 5,885,293 | A | 3/1999 | McDevitt |
| 5,895,390 | A | 4/1999 | Moran et al. |
| 5,904,717 | A | 5/1999 | Brekke et al. |
| 5,918,604 | A | 7/1999 | Whelan |
| 5,919,196 | A | 7/1999 | Bobic et al. |
| 6,007,496 | A | 12/1999 | Brannon |
| 6,017,348 | A | 1/2000 | Hart et al. |
| 6,110,178 | A | 8/2000 | Zech et al. |
| 6,146,385 | A | 11/2000 | Torrie et al. |
| 6,179,839 | B1 | 1/2001 | Weiss et al. |
| 6,179,871 | B1 | 1/2001 | Halpern |
| 6,187,329 | B1 | 2/2001 | Agrawal et al. |
| 6,231,577 | B1 * | 5/2001 | Canedy .................... 606/79 |
| 6,242,247 | B1 | 6/2001 | Rieser et al. |
| 6,280,447 | B1 | 8/2001 | Marino et al. |
| 6,358,253 | B1 | 3/2002 | Torrie et al. |
| 6,375,658 | B1 | 4/2002 | Hangody et al. |
| 6,387,693 | B2 | 5/2002 | Rieser et al. |
| 6,395,011 | B1 | 5/2002 | Johanson et al. |
| 6,442,814 | B1 | 9/2002 | Landry et al. |
| 6,458,144 | B1 | 10/2002 | Morris et al. |
| 6,488,033 | B1 | 12/2002 | Cerundolo |
| 6,528,052 | B1 | 3/2003 | Smith et al. |
| 6,530,928 | B1 | 3/2003 | Frei et al. |
| 6,557,226 | B1 | 5/2003 | Landry et al. |
| 6,591,581 | B2 | 7/2003 | Schmieding |
| 6,592,588 | B1 | 7/2003 | Bobic et al. |
| 6,607,534 | B2 | 8/2003 | Bonutti |
| 6,613,054 | B2 | 9/2003 | Scribner et al. |
| 6,685,709 | B2 | 2/2004 | Sklar |
| 6,696,073 | B2 | 2/2004 | Boyce et al. |
| 6,727,224 | B1 | 4/2004 | Zhang et al. |
| 6,740,484 | B1 | 5/2004 | Khirabadii et al. |
| 6,796,977 | B2 | 9/2004 | Yap et al. |
| 6,835,377 | B2 | 12/2004 | Goldberg et al. |
| 6,852,114 | B2 | 2/2005 | Cerundolo |
| 6,962,592 | B2 | 11/2005 | Gatturna et al. |
| 7,231,815 | B2 | 6/2007 | Kanare |
| 7,241,316 | B2 | 7/2007 | Evans et al. |
| 7,347,130 | B2 | 3/2008 | Pham et al. |
| 2001/0027322 | A1 | 10/2001 | Bowman |
| 2001/0039455 | A1 | 11/2001 | Simon et al. |
| 2002/0022847 | A1 | 2/2002 | Ray, III et al. |
| 2002/0082704 | A1 | 6/2002 | Cerundolo |
| 2002/0095214 | A1 | 7/2002 | Hyde |
| 2003/0009218 | A1 | 1/2003 | Boucher et al. |
| 2003/0130662 | A1 | 7/2003 | Michelson |
| 2003/0212435 | A1 | 11/2003 | Gold et al. |
| 2004/0106928 | A1 | 6/2004 | Ek |
| 2004/0162622 | A1 | 8/2004 | Simon et al. |
| 2004/0210227 | A1 | 10/2004 | Trail et al. |
| 2004/0230303 | A1 | 11/2004 | Gomes et al. |
| 2005/0064042 | A1 | 3/2005 | Vunjak-Novakovic et al. |
| 2005/0222576 | A1 | 10/2005 | Kick et al. |
| 2006/0142775 | A1 | 6/2006 | Heneberry et al. |
| 2007/0093896 | A1 | 4/2007 | Malinin |
| 2007/0135917 | A1 | 6/2007 | Malinin |
| 2007/0135918 | A1 | 6/2007 | Malinin |
| 2007/0135928 | A1 | 6/2007 | Malinin |
| 2007/0276506 | A1 | 11/2007 | Troxel |
| 2009/0222052 | A1 | 9/2009 | Vandewalle |

FOREIGN PATENT DOCUMENTS

| | | |
|---|---|---|
| WO | WO-9106246 | 5/1991 |
| WO | WO-2004103224 | 12/2004 |

OTHER PUBLICATIONS

"Techniques for ACL Reconstruction with Multi-Trac™ Drill Guide," available by 2000.

Acufex Microsurgical, Inc., "Endoscopic Technique for ACL Reconstruction with Pro-Trac Tibial Guide: Endobutton Fixation," available by 2000.

Arthrex, "Osteochondral Autograft Transfer System (OATS), Key Words: Chondral defects, osteochondral cylinder transplants, arthroscopic technique, chronic ACL deficiency" © Arthrex Inc.,1996 (1 page).

Arthrex, Osteochondral Autograft Transfer System (OATS)™, "Surgical Technique," 1996 (pp. 1-24).

Arthrotek® OCD System, Osteochondral Defect Surgical Technique, brochure, © 1999 (4 pages).

Chu et al., Articular Cartilage Transplantation—Clinical Results in the Knee, clinical Orthopaedics and Related Research, No. 360, pp. 159-168 Lippincott, Williams 8 Wilkins, (Mar. 1999).

Convery et al., "Long-Term Survival of Chondrocytes in an Osteochondral Articular Cartilage Allograft," Journal of Bone and Joint Surgery, vol. 78-A, No. 7, pp. 1082-1088 (Jul. 1996).

Gross, M.D., Allan, "Cartilage Resurfacing Filling Defects," The Journal of Arthroplasty vol. 18 No. 3 Suppl. 1 (2003) pp. 14-17.

Hangody et al., Autologous Osteochondral Mosaicplasty for the Treatment of Full-Thickness Defects of Weight-Bearing Joints, Journal of Bone and Joint Surgery, vol. 85-a, Supp. 2, pp. 25-32 (2003).

Hangody, et al., "Arthroscopic autogenous osteochondral mosaicplasty for the treatment of femoral condylar articular defects, A preliminary report," Knee, Surg, Sports Traumatol, Arthrosc (1997) © Springer-Verlag 1997 5:262-267.

Hangody, M.D., et al., "MosaicPlasty™ Osteochondral Grafting Technique Guide", Smith & Nephew Endoscopy, © 1996.

Innovasive Cor™ System, © 1997 Innovasive Devices, Inc. (2 pages).

Instrument Makar, Inc., "Bone Grafters Surgical Technique," Dec. 1995.

Instrument Makar, Inc.,"New Directions in Arthroscopic Innovation," 1991 Catalogue.

Jakob, M.D., Roland, et al., "Autologous Osteochondral grafting in the Knee: Indication, Results, and Reflections," Clinical Orthopaedics and Related Research No. 401, (2002) pp. 170-184.

Malinin, T., M.D., Human Cadaver Femoral Head Homografts for Anterior Cervical Spine Fusions, Reprinted from Surgical Neurology, vol. 7, No. 4, Apr. 1977, Copyright, © 1977.

Malinin, T.I., "University of Miami Tissue Bank: Collection of Postmortem Tissues for Clinical Use and Laboratory Investigation", From the Departments of Surgery and Pathology, University of Miami School of Medicine and the Veterans Administration Hospital, Transplantation Proceedings, vol. VIII, No. 2, Supplement 1 Jun. 1976 (pp. 53-58).

Malinin et al., "Articular Cartilage Nutrition is Mediated by Subchondral Bone: a Long-Term Autograft Study in Baboons," Osteoarthritis and Cartilage, vol. 8, pp. 483-491, OsteoArthritis Research Society Intl. (2000).

Malinin et al., Hypothermic Storage and Cryopreservation of Cartilage, Clinical Orthopedics and Related Research, No. 197, pp. 1526 (Jul.-Aug. 1985).

Matsusue, Y., et al., "Arthroplasty using Mosaicplasty,", NCBI Pub Med, www.ncbi.nlm.nih.gov/entrez/query.fcgi?CMD=Display&DB=pubmed [printed May 29, 2007].

Szerb, M.D., et al., "Mosaicplasty, Long-Term Follow-Up," Bulletin of the Hospital for Joint Diseases, vol. 63, Nos. 1 & 2 (2005), pp. 54-62.

Williams et al.. "Prolonged Storage Effects on the Articular Cartilage of Fresh Human Osteochondral Allografts," Journal of Bone and Joint Surgery, vol. 85-A, No. 1 1, pp. 21 11-21 20 (Nov. 2003).

Christel, P. et al. "Osteochondral Grafting Using Mosaicplasty Technique" downloaded from: www.maitrise-orthop.com/corpusmaitri/orthopaedic/mo76_mosaicplasty/index.shtml (23 pages) on Mar. 23, 2005.

* cited by examiner

SYSTEM FOR FORMING A TENDON-BONE GRAFT

FIELD

The present disclosure relates generally to ligament reconstruction surgery, and more specifically, to systems and methods for forming a tendon-bone graft.

BACKGROUND

The statements in this section merely provide background information related to the present disclosure and may not constitute prior art.

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. During these procedures, surgeons can use orthopedic implants to restore function to the site and facilitate the natural healing process.

Current orthopedic implants are generally composed of non-resorbable metals, ceramics, polymers, and composites. However, in some instances, it may be desirable to have an implant made from donor tissues. For example, in the case of an anterior cruciate ligament (ACL) reconstruction, surgeons can implant a tendon-bone graft. The tendon-bone graft can be recovered from the Achilles tendon/calcaneus or from the patella/patellar ligament/tibia portions of donor tissue. Prior to implantation, the donor bone may be formed into a cylindrical shape so that it can be inserted into a drilled tunnel in the anatomy. Typically, the surgeon carves the bone block into the cylindrical shape, as the presence of the ligament on one side of the bone block makes clamping and conventional cutting techniques impractical.

SUMMARY

A system for forming a bone graft, such as a tendon-bone graft is provided. The system can include at least one support that is adapted to support the tendon-bone graft. The system can further include at least one clamp that is adapted to engage the tendon-bone graft to clamp the tendon-bone graft to the at least one support. The system can also include at least one cutting member that is operable to resect the tendon-bone graft. The at least one cutting member or the at least one support can be moveable relative to the other of the at least one cutting member or the at least one support to resect the tendon-bone graft. The system can also include a means of protecting the tendon so that the tendon is not damaged during the resection of the bone graft.

Further provided is a method for forming a tendon-bone graft. The method can include placing a tendon-bone graft in a support and applying a first clamping force to clamp the tendon-bone graft in the support. The method can also include moving a cutting member substantially perpendicular to the first clamping force to resect a first side of the tendon-bone graft, and moving the cutting member substantially perpendicular to the first clamping force to resect a second side of the tendon-bone graft. The method can include removing the first clamping force from the tendon-bone graft and applying a second clamping force to the first side and second side of the tendon-bone graft. The method can also include moving a cutting member perpendicular to the second clamping force to resect a third side of the tendon-bone graft.

A broach for shaping a tendon-bone graft is also provided. The broach can include a broach housing formed on a longitudinal axis with a proximal end and a distal end for holding a plurality of broach teeth. Each broach tooth can have a cutting arc in the range from about 30 degrees to about 315 degrees that can be contoured to preserve a tendon. A first broach tooth can be carried in the broach housing toward the distal end, and the first broach tooth can have a first size configured for a first shaving of a tendon-bone graft. A second broach tooth can be carried in the broach housing. The second broach tooth can have a second size that is at least 0.005 inch smaller than the first size, and can be configured for a second shaving of the tendon-bone graft. A third broach tooth can be carried in the broach housing toward the proximal end. The third broach tooth can have a third size that is at least 0.005 inch smaller than the second size configured for a third shaving of the tendon-bone graft.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. Although the following description can be related generally to a tendon-bone graft forming system that can be used to sculpt or resect a tendon-bone graft prior to positioning the tendon-bone graft in a prepared portion of the anatomy, such as in a femur and tibia, it will be understood that the tendon-bone graft forming system, as described and claimed herein, can be used to sculpt or resect any appropriate graft. Therefore, it will be understood that the following discussions are not intended to limit the scope of the appended claims.

Figure 1:
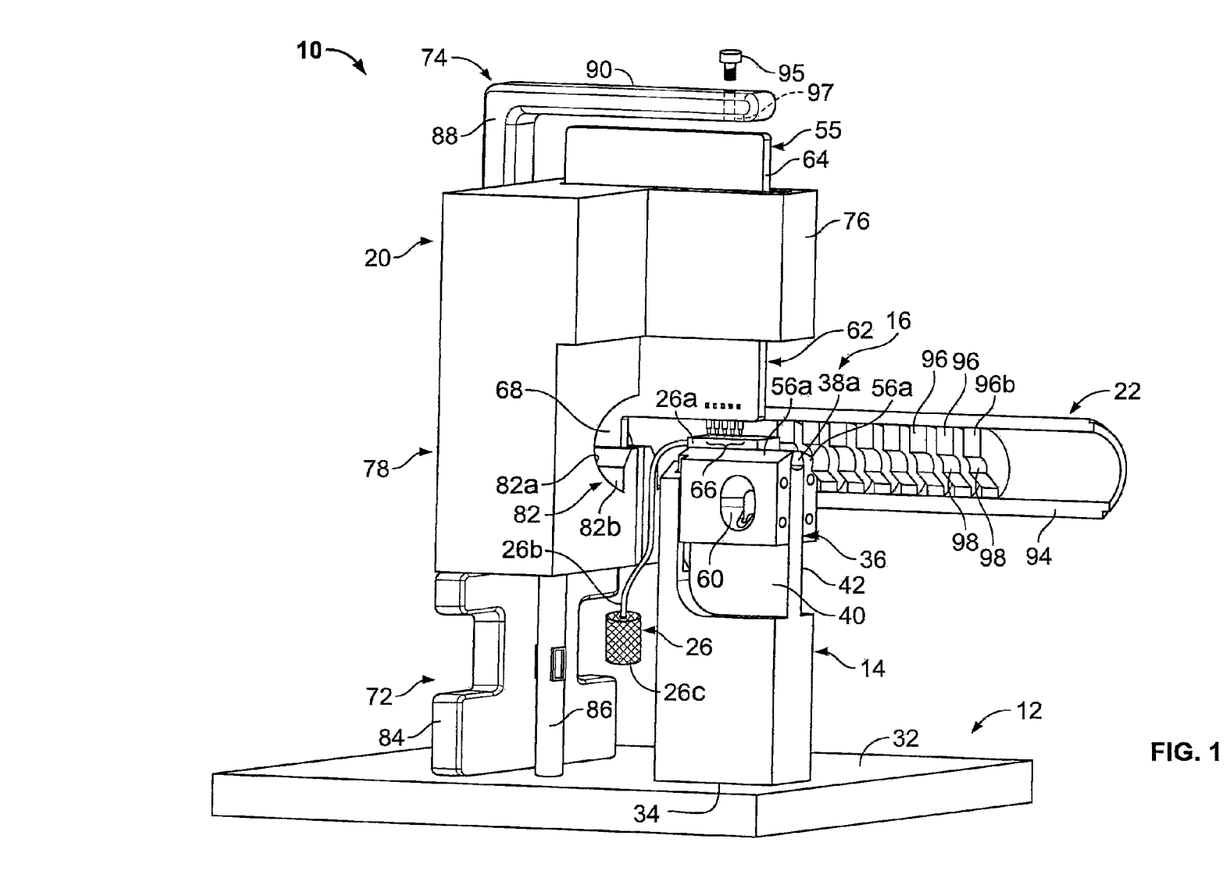
FIG. 1 is a perspective schematic view of a system for forming a tendon-bone-bone graft according to the present disclosure in which all components are assembled to the system.

With reference to FIG. 1, a graft forming system 10 is shown. The system 10 can include a base 12, at least one support 14, at least one clamp or a clamp system 16, a guide 20 and at least one cutting member 22. The system 10 can be composed of any suitable sterilizable material, such as a metal or metal alloy. The system 10 can enable a user to form a tendon-bone graft 26. The tendon-bone graft 26 can include at least one bone block 26a and a tendon 26b. The system 10 can be used to form the bone block 26a into a desired shape, such as a cylinder 26c, prior to the insertion of the tendon-bone graft 26 into an anatomy.

The base 12 can be any suitable member or surface to which the support 14, clamp system 16, guide 20 and cutting member 22 can be operatively coupled. As the base 12 can comprise any suitable sterilizable member or surface, the base 12 will not be discussed in great detail herein. In addition, it should be understood that the base 12 can be optional, and the support 14, clamp system 16, guide 20 and cutting member 22 can be operatively coupled to an operating table or other structure in the operating room, such as a tray. Briefly, however, the base 12 can include a surface 32. At least the support 14 and the guide 20 can be coupled to the surface 32.

Figure 2:
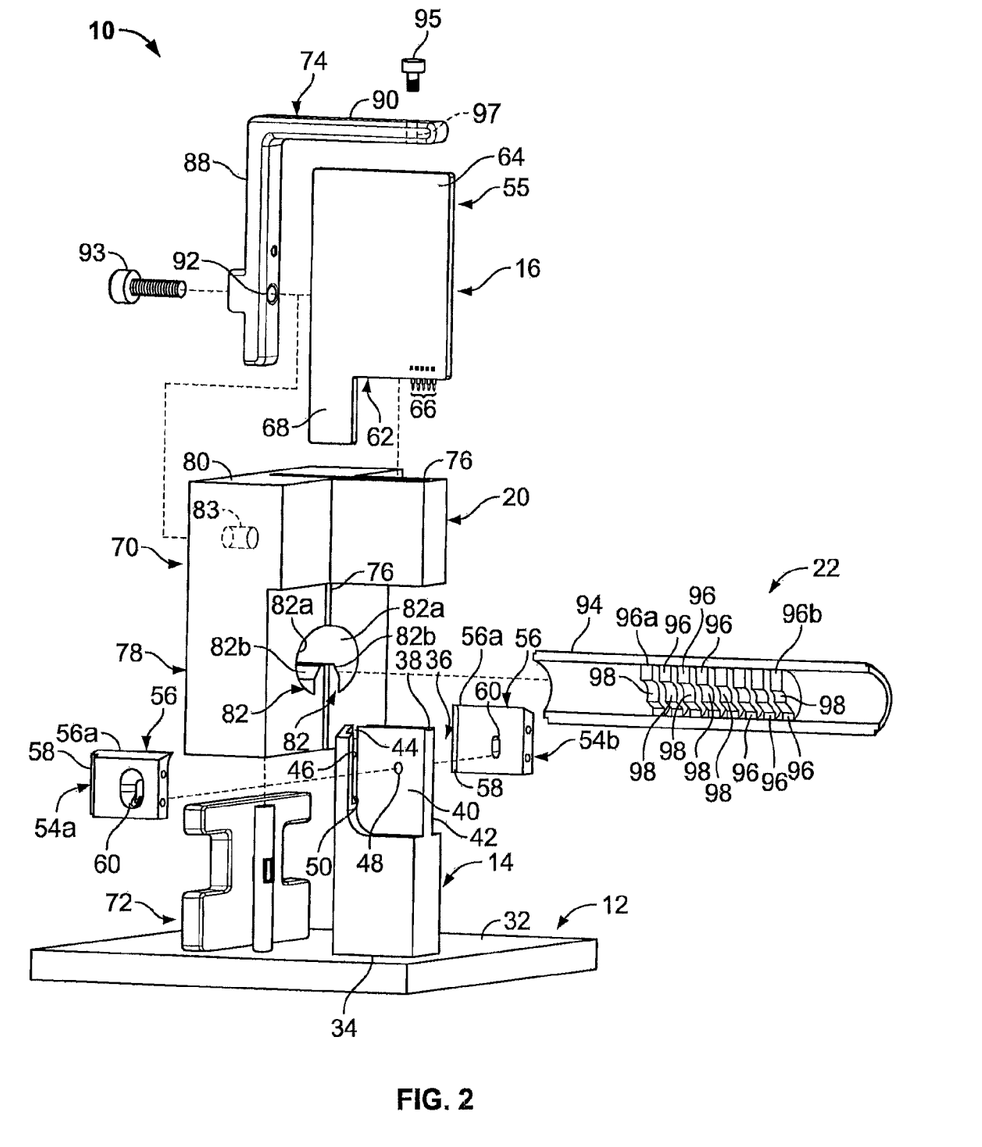
FIG. 2 is an exploded view of the system of FIG. 1.

With reference to FIGS. 1 and 2, the support 14 can include a distal end 34 and a proximal end 36. The support 14 can be formed of any suitable sterilizable material, such as a metal or metal alloy. The distal end 34 can be coupled to the base 12. The proximal end 36 can support the bone block 26a. The proximal end 36 can include a bone holding surface 38, a first side or slot 40, a second side or slot 42 and a tendon support 44 (FIG. 2) that creates a space or relief for the tendon 26b to rest to prevent damage to the tendon while the bone block 26a is being formed by the cutting member 22. The bone holding surface 38 can have a curved surface 38a and can assist in retaining the bone block 26a on the support 14 during the resection of the bone block 26a. It should be understood that although the bone holding surface 38 is described herein as having the curved surface 38a, the bone holding surface 38 can have any appropriate contour, such as flat, convex, concave, etc. The bone holding surface 38 can prevent the bone block 26a from moving during the resection of the bone block 26a, as will be discussed.

The first slot 40 can be formed opposite the second slot 42, such that the bone holding surface 38 is disposed between the first slot 40 and the second slot 42. The first slot 40 can be a mirror image of the second slot 42, and thus, the same reference numerals will be used for the features of the first slot 40 and second slot 42. The first slot 40 and the second slot 42 can couple the clamp system 16 to the proximal end 36 of the support 14. Both the first slot 40 and the second slot 42 can define a channel 46 and a bore 48. The channel 46 can enable the clamp system 16 to slideably engage the first slot 40 and second slot 42, as will be discussed, and the bore 48 can receive a mechanical fastener, such as a screw, bolt, etc. to couple the clamp system 16 to the first slot 40 and/or second slot 42. The channel 46 can be defined within the first slot 40 and second slot 42 to enable the clamp system 16 to be positioned between a first, engaged position and a second, disengaged position. In the first, engaged position, the clamp system 16 can be coupled to the proximal end 36 such that the clamp system 16 can be secured to engage the bone block 26a to hold the bone block 26a during the resection of the bone block 26a. In the second, disengaged position, the clamp system 16 can be positioned at an end 50 of the channel 46 or removed from the support 14 entirely. The channels 46 can also include an angular projection 52 that can define the tendon support 44.

The tendon support 44 can be defined by and between the angular projection 52 of each of the first slot 40 and the second slot 42, as best shown in FIG. 2. In this regard, the angular projections 52 of each of the first slot 40 and the second slot 42 can define an aperture for receipt of the tendon 26b. Generally, the angular projection 52 of the first slot 40 can be spaced from the angular projection 52 of the second slot 42 by a distance substantially equivalent to the width of the bone holding surface 38. Thus, the tendon support 44 can generally be defined planar to the bone holding surface 38 so that when the bone block 26a is disposed on the bone holding surface 38, the tendon 26b can be retained within and protected by the tendon support 44, as will be discussed.

The clamp system 16 can include at least one clamp 54 and a clamp blade 55. Generally, the at least one clamp 54 can include a first clamp 54a and a second clamp 54b. Each of the first clamp 54a, second clamp 54b and clamp blade 55 can selectively engage the bone block 26a during the resection of the tendon-bone graft 26 to hold the bone block 26a in place on the support 14. The first clamp 54a and the second clamp 54b can be coupled to the support 14, while the clamp blade 55 can be coupled to the guide 20.

Figure 5:
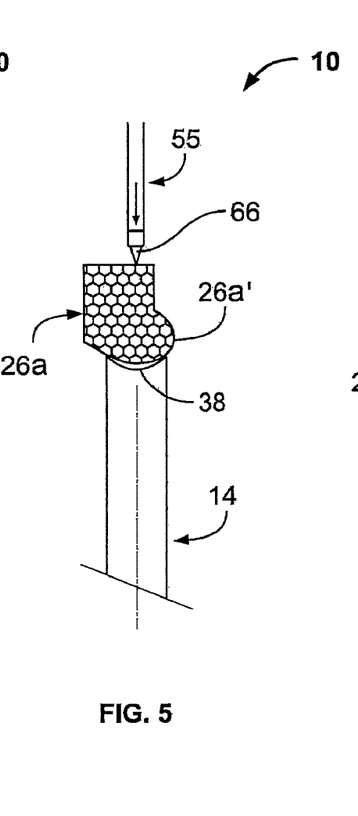
FIG. 5 is a simplified schematic view of a procedure for forming a tendon-bone-bone graft using the system of FIG. 1.

The first clamp 54a can be substantially identical to the second clamp 54b, and thus, the same reference numerals will be used to refer to features of both the first clamp 54a and second clamp 54b. Both the first clamp 54a and the second clamp 54b can include a proximal end 56, a rib 58 and a bore 60. The proximal end 56 can include an angled tip 56a. The angled tip 56a can be configured to engage a resected surface 26a' of the bone block 26a to enable the final resection of the bone block 26a, as will be discussed herein (FIG. 5). The rib 58 can be configured to slideably engage the channel 46 to enable the first clamp 54a and second clamp 54b to move relative to the support 14 between the first, engaged position and the second, disengaged position. The bore 60 can receive a mechanical fastener, such as a screw, bolt, pin, etc., to couple the respective first clamp 54a or second clamp 54b to the support 14. It should be noted that the bores 60 of the first clamp 54a and second clamp 54b can receive a single mechanical fastener therethrough to couple both the first clamp 54a and the second clamp 54b to the support 14 in the first, engaged position.

The clamp blade 55 can be slideably coupled to the guide 20. The clamp blade 55 can include a proximal end 62 and a distal end 64. The proximal end 62 can include at least one bone engagement member 66 and a projection 68. The bone engagement members 66 can comprise any suitable mechanism for engaging the bone block 26a to hold the bone block 26a during resection, such as at least one spike, tooth, cleat, etc. The projection 68 can assist in positioning the cutting member 22 relative to the guide 20, as will be discussed. The distal end 64 can extend beyond the guide 20 when the clamp blade 55 is in a first, engaged position to enable the user to manipulate the clamp blade 55 by grasping the distal end 64. For example, the user can pull the clamp blade 55 into a second, disengaged position in which the clamp blade 55 is removed from the slot 76 by grasping the distal end 64.

The guide 20 can include a body 70, a support system 72 and a lock 74. The guide 20 can assist the user in properly aligning the cutting member 22 with respect to the bone block 26a. The body 70 can be supported by the support system 72, and the lock 74 can secure the clamp blade 55 within the body 70 of the guide 20.

The body 70 can include a slot 76, a proximal end 78 and a distal end 80. The body 70 can be formed with a generally L-shape, with the proximal end 78 extending vertically adjacent to the support 14. The slot 76 can have a width sized to enable the clamp blade 55 to be slideably received within the guide 20. Generally, the slot 76 can extend from the proximal end 78 to the distal end 80 to enable the bone engagement members 66 of the clamp blade 55 to securely engage the bone block 26a.

The proximal end 78 can define two apertures 82. The apertures 82 can be generally semi-circular in shape, and can each include an arcuate surface 82a and a lip 82b. The apertures 82 can guide the cutting member 22 during the resection of the bone block 26a. The apertures 82 can comprise mirror images to guide the cutting member 22 during resection of both sides of the bone block 26a. The arcuate surfaces 82a can have a radius of curvature substantially equivalent to a radius of curvature of the cutting member 22 such that the cutting member 22 can slideably engage the apertures 82. The lip 82b can be shaped to correspond to a cutting surface of the cutting member 22 to enable the cutting member 22 to pass through the apertures 82 without damaging the body 70. Generally, the apertures 82 can be formed on the proximal end 78 such that when the guide 20 is assembled to the base 12, the lip 82b of each of the apertures 82 is substantially coplanar and laterally aligned with the proximal end 36 of the support 14. The proximal end 78 of the body 70 can contact the support system 72, which can be used to raise or lower the body 70 relative to the support 14 to further align the apertures 82 with the support 14, if necessary. By being sized to slideably engage the cutting member 22, the apertures 82 can ensure the proper formation of the tendon-bone graft 26 by maintaining the proper alignment of the cutting member 22 relative to the bone block 26a.

The distal end 80 of the body 70 can include a bore 83, as shown in FIG. 2. The bore 83 can couple the lock 74 to the body 70 of the guide 20. The bore 83 can generally be threaded to receive a mechanical fastener, such as a bolt, screw, etc, however, it will be understood that any suitable fastening element could be employed to couple the lock 74 to the body 70, such as a pin.

Figure 3:
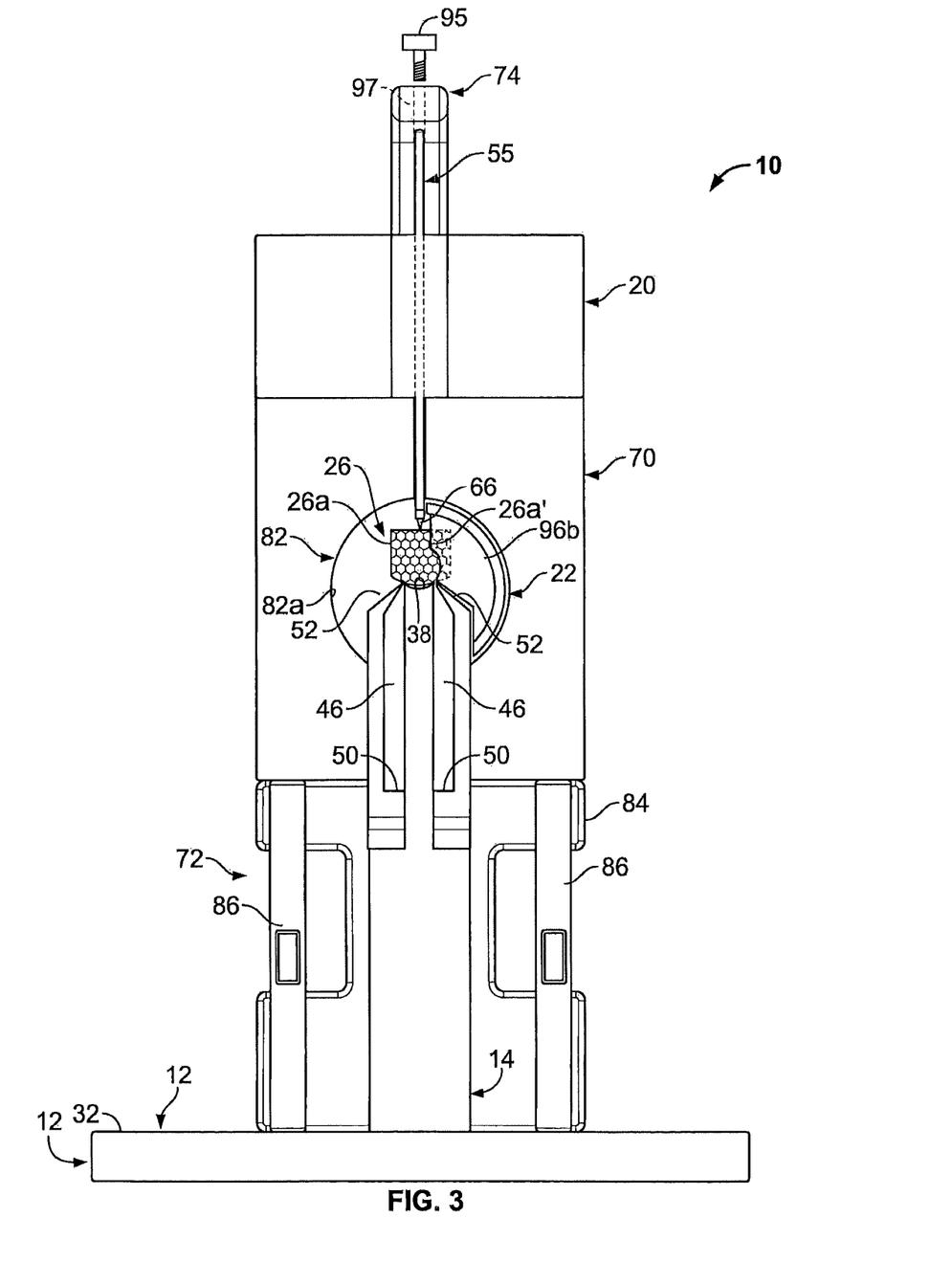
FIG. 3 is a schematic side view of a procedure for forming a tendon-bone-bone graft using the system of FIG. 1.

The support system 72 can include a support block 84 and at least one support beam 86 as shown in FIGS. 2 and 3. The support system 72 can be optional, and if employed, can cooperate with the support 14 to raise the body 70 to such a height that enables the ergonomic resection of the bone block 26a. The support block 84 and support beam(s) 86 can be substantially the same height to provide uniform support to the body 70 of the guide 20. The support block 84 is illustrated as including two notched regions, however, it will be understood that the support block 84 can have any suitable shape or configuration, and for example, can be rectangular, square, L-shaped, H-shaped, C-shaped and the like. Further, although the support block 84 and support beam(s) 86 are illustrated as being discrete elements, the support block 84 and/or the support beam(s) 86 could be integrally formed to comprise a single element or could be integrally formed with the body 70 of the guide 20, if desired. The support beam(s) 86 can comprise two support beams 86, however, any suitable number of support beam(s) 86 could be employed (FIG. 3).

With reference to FIGS. 1-3, the lock 74 can be coupled to the distal end 80 of the body 70. The lock 74 can secure the clamp blade 55 within the slot 76 of the body 70. In this regard, the lock 74 can ensure that the clamp blade 55 remains fixedly engaged with the bone block 26a during the resection of the bone block 26a. The lock 74 can be generally L-shaped, and can include a first member 88 and a second member 90. The first member 88 can define a bore 92. The bore 92 can receive a mechanical fastener 93, such as a screw, bolt, pin, etc., to couple the lock 74 to the body 70. The second member 90 can extend perpendicular to the first member 88, and can extend over the distal end 64 of the clamp blade 55. The second member 90 can define an aperture 97 that can receive a mechanical fastener 95, such as a screw, bolt, pin, etc., to prevent the clamp blade 55 from backing out of the slot 76 during the resection of the bone block 26a.

The cutting member 22 can be operable to resect the bone block 26a and can be slideably received within the apertures 82 of the body 70. The cutting member 22 can include a half pipe 94 and at least one resecting member or broach tooth 96. The cutting member 22 can progressively resect the bone block 26a to sculpt the BTB graft 26 into a cylinder 26c (FIG. 1). Generally, the cutting member 22 can be advanced in a direction perpendicular to a clamp force generated by the clamp system 16. For example, if the clamp blade 55 is engaged with the bone block 26a to clamp the bone block 26a to the bone holding surface 38, the clamp force can be generated generally vertically, parallel to the support 14, and the cutting member 22 can be advanced perpendicular to the clamp force, and thus, perpendicular to the support 14 and the clamp blade 55.

In another example, if the first clamp 54a and second clamp 54b are engaged with the bone block 26a to clamp the bone block 26a to the bone holding surface 38, then the clamp force can be generated generally vertically parallel to the support 14, and the cutting member 22 can be advanced perpendicular to the first clamp 54a and the second clamp 54b to resect the bone block 26a. The half pipe 94 can be semi-circular, with the radius of curvature that corresponds with the apertures 82, to enable the cutting member 22 to be slideably received through the apertures 82. The cutting member 22 can be advanced through the apertures 82 using any suitable driving apparatus, manually or powered, such as a hammer or a pneumatic driver. Generally, the cutting member 22 can be advanced axially linearly to the bone block 26a. The at least one broach tooth 96 can comprise a plurality of broach teeth 96 that can be coupled to the half pipe 94. The broach teeth 96 can have a cutting surface 98 that decreases in radius from a proximal broach tooth 96a to a distal broach tooth 96b to provide a progressive cutting surface that gradually or incrementally resects the bone block 26a.

In this regard, each broach tooth 96 can have a cutting surface 98 that forms an arc in the range from about 30 degrees to about 315 degrees. This cutting surface 98 can be contoured to preserve and protect the tendon 26b during the resection of the bone block 26a. Generally, the cutting surface 98 of each broach tooth 96 can cut a partial cylinder into the bone block 26a, with the distal broach tooth 96b cutting the partial cylinder with a final radius equivalent to a desired radius of the cylinder 26c. For example, the proximal broach tooth 96a can have a cutting surface 98 that performs a first shaving, while a second broach tooth 96 adjacent to the proximal broach tooth 96a can have a cutting surface 98 that can be at least about 0.005 inches smaller than the cutting surface 98 of the proximal broach tooth 96a to enable a second shaving of the bone block 26a. Similarly, for example, a third broach tooth 96 can be adjacent to the second broach tooth 96, and the third broach tooth can have a third cutting surface 98 that can be at least about 0.005 inches smaller than the second cutting surface 98 to enable a third shaving of the bone block 26a. It will be understood, however, that the cutting surface 98 could have any desired shape to resect the bone block 26a into any desired shape, such as rectangular, triangular, pentagonal, etc.

With reference now to FIG. 3, with the clamp blade 55 out of the slot 76, the tendon-bone graft 26 can be placed on the bone holding surface 38 such that the tendon 26b is supported on the tendon support 44 (best illustrated in FIGS. 1 and 2). Then, the clamp blade 55 can be inserted into the slot 76 so that the bone engagement members 66 can engage the bone block 26a, as shown in FIG. 3. If desired, a force can be applied to the distal end 60 of the clamp blade 55 to impact the bone engagement members 66 with the bone block 26a (not shown). When the clamp blade 55 is properly positioned within the slot 76 of the guide 20, the lock 74 can be secured to the body 70 of the guide 20 to prevent the clamp blade 55 from backing out of the slot 76. The clamp blade 55 in combination with the bone holding surface 38 can provide a stable three point contact to hold and retain the bone block 26a in a stable position while still enabling the bone block 26a to be shaped by the cutting member 22.

Figure 4:
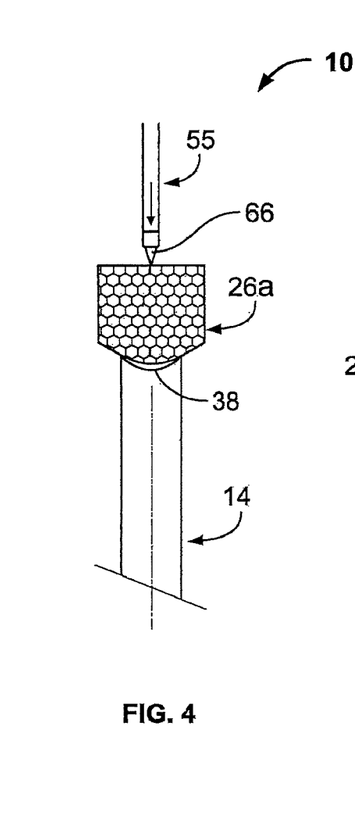
FIG. 4 is a simplified schematic view of a procedure for forming a tendon-bone-bone graft using the system of FIG. 1.

In order to begin resecting the bone block 26a, with the bone engagement members 66 engaged with the bone block 26a, the cutting member 22 can be inserted into a first one of the apertures 82. With the cutting member 22 inserted into the desired aperture 82, the user can advance the cutting member 22 (manually or power-assisted) so that the broach teeth 96 can resect the bone block 26a (shown in phantom) to form a resected surface 26a'. In this regard, with reference to FIG. 4, a simplified schematic view illustrates the bone block 26a prior to resection. With reference to FIG. 5, after the cutting member 22 is advanced linearly through the guide 20, perpendicular to the clamp force, the resected surface 26a' can be formed, which can comprise a cylindrical surface. After the distal broach tooth 96b has contacted and resected one side of the bone block 26a, the cutting member 22 can be removed from the aperture 82.

During the resection of the bone block 26a, the lip 82b of the aperture 82 and the projection 68 of the clamp blade 55 can protect the tendon 26b from damage by the cutting member 22. The clamp blade 55 and the bone holding surface 38 can stablize the bone block 26a during the resection, while providing enough clearance to appropriately shape the bone block 26a as desired.

Figures 6, 7:
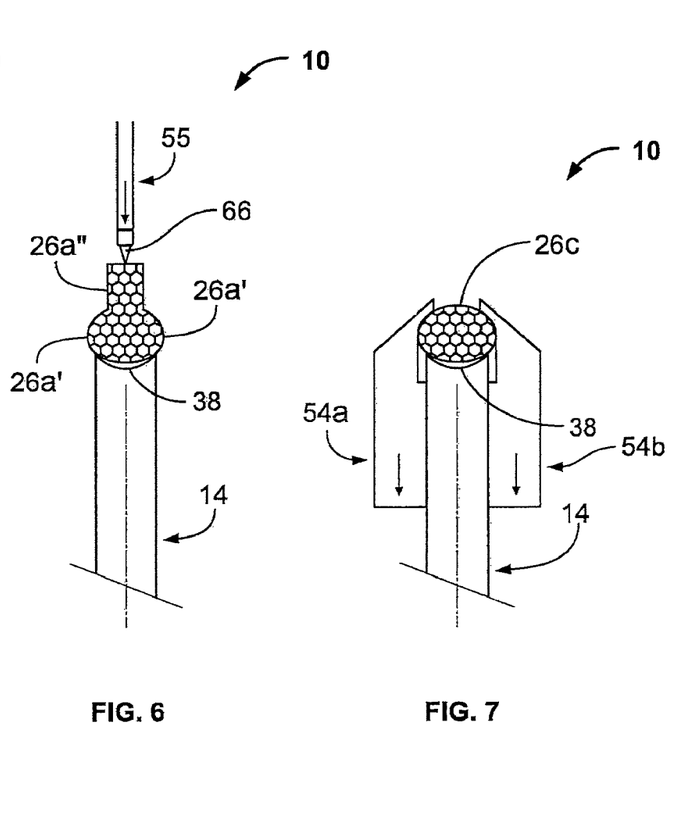
FIG. 6 is a simplified schematic view of a procedure for forming a tendon-bone graft using the system of FIG. 1.
FIG. 7 is a simplified schematic view of a procedure for forming a tendon-bone graft using the system of FIG. 1.

The cutting member 22 can be inserted in the remaining aperture 82, to resect a second side of the bone block 26a, as shown schematically in FIG. 6. The cutting member 22 can be axially or linearly advanced until the distal broach tooth 96b contacts and resects the bone block 26a to form the resected surface 26a' on the side of the bone block 26a. Then, the cutting member 22 can be removed from the respective aperture 82. Since the sides of the bone block 26a have been cut into partial cylinders by the cutting member 22 as shown in FIG. 6, a top surface 26a" of the bone block 26a can remain.

The top surface 26a" can be resected to form the cylinder 26c and to remove any indentations caused by the engagement of the bone engagement members 66 of the clamp blade 55 with the bone block 26a, as shown in FIG. 7. In order to resect the top surface 26a", the first clamp 54a and the second clamp 54b can be moved into the first, engaged position and secured with an appropriate mechanical fastener (not shown). Generally, the first clamp 54a and the second clamp 54b can have appropriately shaped contact areas such that the first clamp 54a and second clamp 54b can be coupled to the support 14 without damaging the bone block 26a. In the first, engaged position, the angled tip 56a of the first clamp 54a and the second clamp 54b can engage the resected surfaces 26a' of the bone block 26a and can hold the bone block 26a against the bone holding surface 38.

Then, the lock 74 can be disconnected from the body 70 of the guide 20. The clamp blade 55 can be moved into the second, disengaged position by pulling the clamp blade out of engagement with the bone block 26a, and removing the clamp blade 55 from the slot 76. Then, the cutting member 22 can be rotated such that the cutting member 22 is parallel to the top surface 26a" of the bone block 26a. Once aligned properly with the top surface 26a", the cutting member 22 can be partially inserted into both apertures 82 such that the engagement of the cutting member 22 with the apertures 82 can guide the cutting member 22 to resect the top surface 26a" of the bone block 26a to form the cylinder 26c, as shown schematically in FIG. 6. It should be understood, however, that the cutting member 22 need not necessarily be employed to resect the top surface 26a", rather, any suitable cutting member could be employed, such as a broach with centralized cutting teeth (not shown), a bone saw, etc. Once the top surface 26a" is resected, the first clamp 54a and the second clamp 54b can be uncoupled from the support 14 to release the cylinder 26c from the support 14. Then, if desired, the system 10 can be used to resect a second bone block of the tendon-bone graft 26. Otherwise, the tendon-bone graft 26 can be inserted into a prepared anatomy (not shown).

Figure 8:
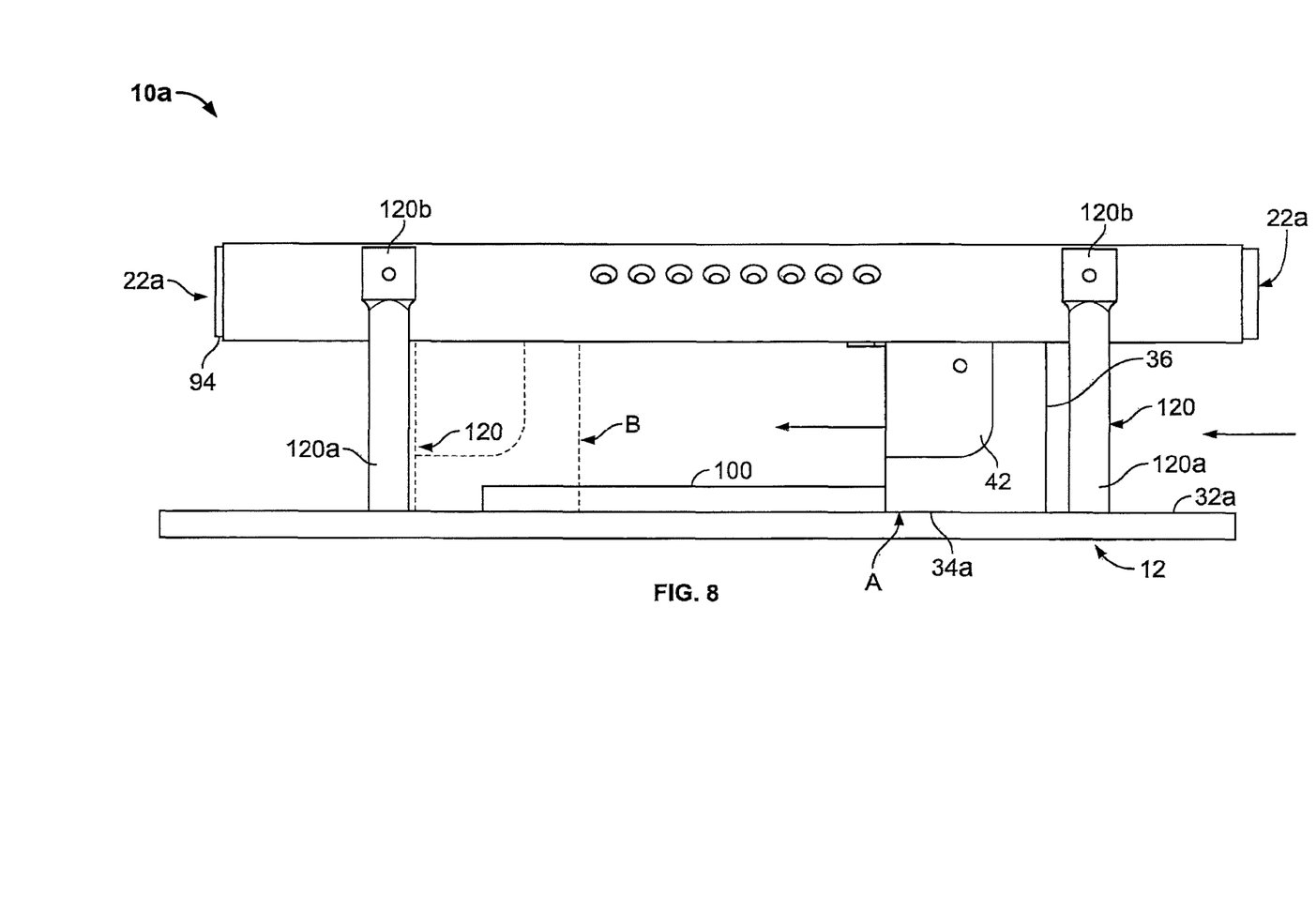
FIG. 8 is side schematic view of a system for forming a tendon-bone graft according to the present disclosure.
Figure 9:
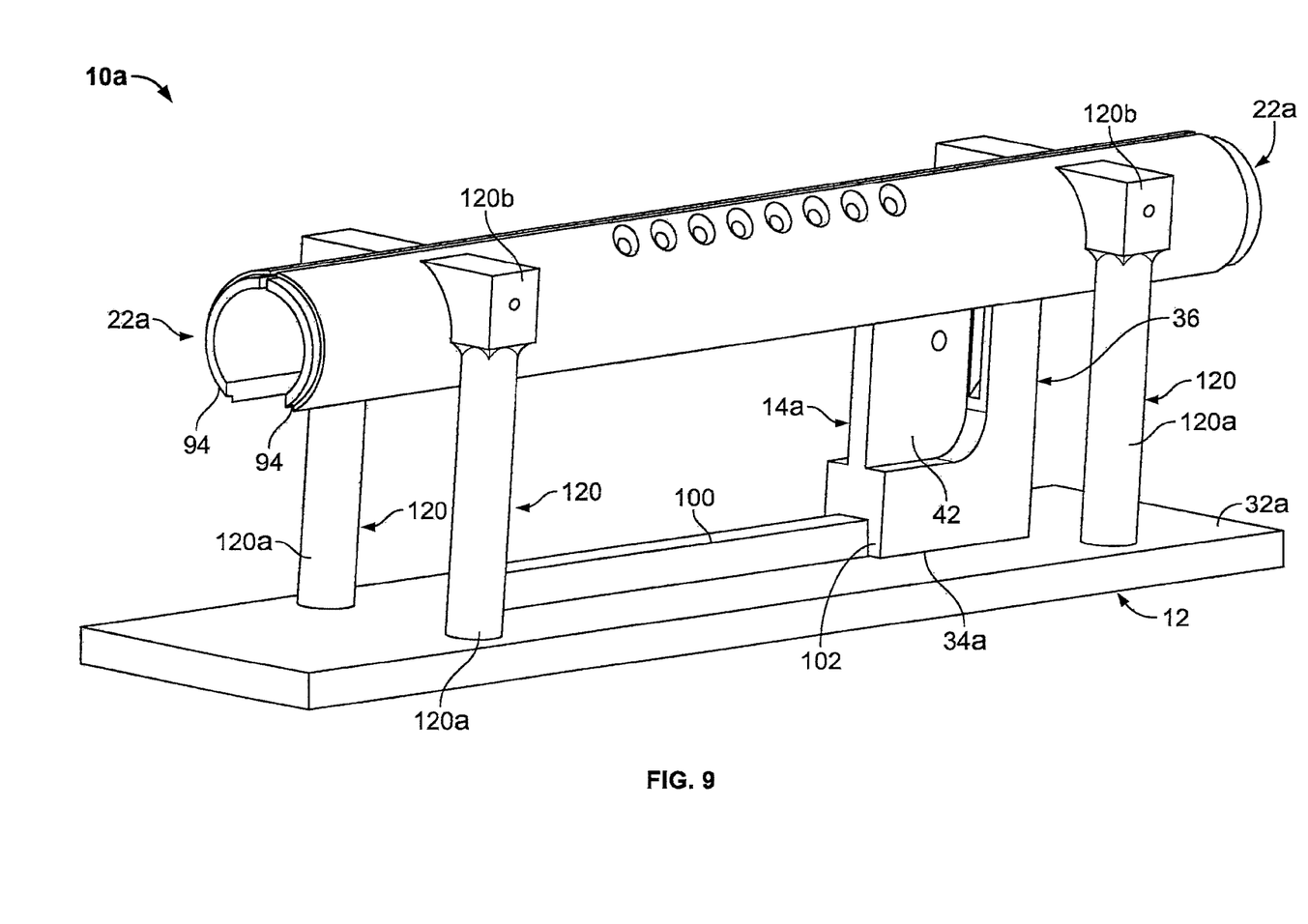
FIG. 9 is a perspective schematic view of the system of FIG. 8.
Figure 10:
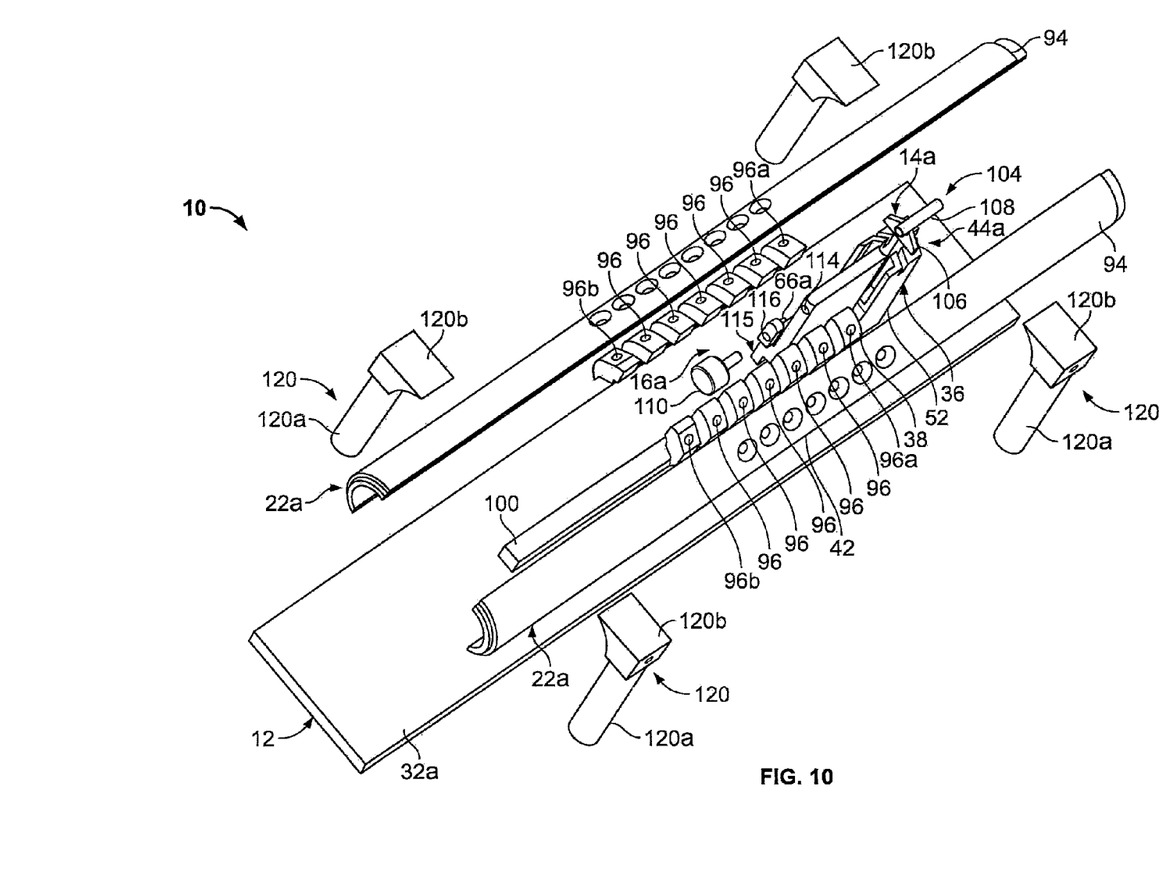
FIG. 10 is an exploded view of the system of FIG. 8.

With reference to FIGS. 8-10, a second graft forming system 10a is shown. As the system 10a can include the same or similar components discussed with regard to FIGS. 1-7, the same reference numerals will be used herein to refer to the same or similar components. The system 10a can include a base 12a, a support 14a, at least one clamp or a clamp system 16a (FIG. 10) and at least one or a plurality of cutting members 22a. The system 10a can be used to form the bone block 26a (shown in phantom in FIG. 8) into a desired shape, prior to the insertion of the tendon-bone graft 26 into an anatomy.

The base 12a can be any suitable member or surface to which the support 14a and cutting members 22a can be operatively coupled. It should be understood, however, that the base 12a can be optional, and the support 14a and cutting members 22a can be operatively coupled to an operating table or other structure in the operating room, such as a tray. As the base 12a of the system 10a can be substantially similar to the base 12 of the system 10 discussed with regard to FIGS. 1-7, the base 12a will not be discussed in great detail herein. Briefly, however, the base 12a can include a surface 32a. The surface 32a can include a guide rail 100. The guide rail 100 can enable the support 14a to move relative to the cutting members 22a, and generally, the guide rail 100 can be formed on the surface 32a such that the support 14a can move in a linear direction parallel to the cutting members 22a to resect the bone block 26a, as will be discussed herein. Thus, the support 14a can be slideably coupled to the guide rail 100.

With continued reference to FIGS. 8-10, the support 14a is shown. As the support 14a of the system 10a can be substantially similar to the support 14 of the system 10 discussed with regard to FIGS. 1-7, the support 14a will not be discussed in great detail herein. Briefly, however, the support 14a can include a distal end 34a and the proximal end 36. As best shown in FIG. 9, the distal end 34a can include a channel 102 to enable the support 14a to slideably engage the base 12a. It should be noted, however, that any technique could be used to slideably couple the support 14a to the base, such as through the use of wheels, bearings, etc., and further, the guide rail 100 could be recessed into the base 12a, if desired, and the support 14a could include a projection to engage the recessed guide rail 100. In any configuration, the distal end 34a and guide rail 100 can cooperate to ensure the proper formation of the tendon-bone graft 26 by maintaining the proper alignment of the support 14a, and thus, the bone block 26a, relative to the cutting members 22a, as will be discussed herein.

The proximal end 36 of the support 14a can support the bone block 26a. The proximal end 36 can include the bone holding surface 38, the first side or slot 40, the second side or slot 42 and a tendon support 44a (FIG. 10). The tendon support 44a can create a space or relief for the tendon 26b (not shown) to rest to prevent damage to the tendon 26b while the bone block 26a is being formed by the cutting members 22a. As the bone holding surface 38, the first slot 40 and the second slot 42 of the support 14a can be substantially similar to the bone holding surface 38, the first slot 40 and the second slot 42 of the support 14 discussed with regard to FIGS. 1-7, the bone holding surface 38, the first slot 40 and the second slot 42 will not be discussed in great detail herein.

The tendon support 44a can be defined by and between the angular projection 52 of each of the first slot 40 and the second slot 42, as best shown in FIG. 10, and as discussed with regard to FIGS. 1-7. In this regard, the angular projections 52 of each of the first slot 40 and the second slot 42 can define an aperture for receipt of the tendon 26b. Generally, the angular projection 52 of the first slot 40 can be spaced from the angular projection 52 of the second slot 42 by a distance substantially equivalent to the width of the bone holding surface 38. Thus, the tendon support 44a can generally be defined planar to the bone holding surface 38 so that when the bone block 26a is disposed on the bone holding surface 38, the tendon 26b can be retained within and protected by the tendon support 44a, as will be discussed.

The tendon support 44a can also include a stop 104 that can further protect the tendon 26b during the resection of the bone block 26a. The stop 104 can include a holding surface 106 and a lever 108. The stop 104 can operate to protect the tendon 26b by securing the tendon 26b within the aperture defined by the angular projections 52 of the first slot 40 and second slot 42. The holding surface 106 of the stop 104 can abut a rear surface of the bone block 26a (not specifically shown) to assist the clamp system 16 in coupling the bone block 26a to the support 14a. The holding surface 106 can also be sized such that a portion of the holding surface 106 can engage the aperture defined by the first slot 40 and second slot 42, which can couple the holding surface 106 of the stop 104 to the support 14a. The lever 108 can enable the user to easily disengage the holding surface 106 from the support 14a. In order to employ the stop 104 with the system 10a, the tendon 26b can be placed into the aperture defined by the angular projections 52, and then the stop 104 can be coupled to the aperture to ensure the tendon 26b remains within the tendon support 44a. Thus, the tendon support 44a, including the stop 104, can protect the tendon 26b from damage during the resection of the bone block 26a.

As best shown in FIG. 10, the clamp system 16a can include a clamp 110 and a bone engagement member 66a. The clamp system 16a can engage the bone block 26a during the resection of the tendon-bone graft 26 to hold the bone block 26a in place on the support 14a. The clamp 110 can comprise a thumbscrew that can threadably engage a threaded aperture 114 defined in a third side 115 of the support 14a. It should be noted, however, that the clamp 110 can comprise any suitable mechanism that can couple the bone block 26a to the support 14a, such as a kotter pin, C-clamp, etc. If the clamp 110 comprises a thumbscrew, then the bone engagement member 66a can define an aperture 116 through which the clamp 110 can pass to secure the bone engagement member 66a, and thus, the bone block 26a to the support 14a. The bone engagement member 66a can comprise any suitable mechanism for engaging the bone block 26a to secure the bone block 26a to the support 14a during the resection of the bone block 26a, such as at least one spike, tooth, cleat, etc.

The cutting members 22a can be operable to resect the bone block 26a. It should be noted that although the cutting members 22a are illustrated herein as comprising two cutting members 22a that are mirror images of each other, it will be understood that the cutting member(s) 22a could comprise a uniform cutting member 22a, if desired. The cutting members 22a can include the half pipe 94, the at least one resecting member or broach tooth 96 and at least one support 120. As the half pipe 94 and the broach tooth or broach teeth 96 of the cutting members 22a can be substantially similar to the half pipe 94 and the broach tooth or broach teeth 96 of the cutting member 22 discussed with regard to FIGS. 1-7, the half pipe 94 and the broach tooth or broach teeth 96 will not be discussed in great detail herein.

Briefly, however, the cutting members 22a can progressively resect the bone block 26a to sculpt the tendon-bone graft 26 into a cylinder 26c, substantially similar to the bone block 26a and cylinder 26c shown in FIG. 1. Generally, the support 14a can be advanced in a linear direction that is parallel to the cutting members 22a to enable the resection of the bone block 26a. The support 14a can be advanced relative to the cutting members 22a via any suitable technique that applies a force sufficient enough to advance the support 14a, such as through the application of an impact force by a hammer, a hydraulic cylinder, pneumatic driver or the like, for example.

The at least one support 120 of the cutting members 22a can generally comprise a plurality of supports 120. The supports 120 can support and couple the cutting members 22a to the base 12a. The supports 120 are illustrated herein as comprising pillars 120a and a curved holding section 120b. It should be understood, however, that the supports 120 could comprise any suitable support structure, such as a block, pegs, etc., and further, the cutting members 22a could be integrally formed with a support structure to enable the cutting members 22a to be directly coupled to the base 12a. Generally, the cutting members 22a can be coupled fixedly to the base 12a via the supports 120, such that the cutting members 22a remain substantially static during the advancement or movement of the support 14a relative to the base 12a and cutting members 22a.

With continued reference to FIGS. 8-10, in order to form the tendon-bone graft 26 using the system 10a, with the support 14a in a first position A on the guide rail 100, the bone block 26a can be positioned on the bone engaging surface 38a of the support 14a. Then, the stop 104 can be positioned in the aperture defined between the first slot 40 and the second slot 42 to secure the tendon 26b within the tendon support 44a. With the tendon 26b protected and retained by the tendon support 44a, the bone block 26a can be coupled to the support 14a with the clamp 110. In this regard, the clamp 110 can be tightened or secured to the support 14a such that the bone engagement member 66a can engage and couple the bone block 26a to the support 14a. The clamp 110 can apply a clamp force to the bone block 26a via the bone engagement feature 66a. The clamp force can be substantially parallel to the guide rail 100, such that the clamp force can be generated in a direction that is parallel to the path of travel of the support 14a. It should be noted, however, that if a C-clamp is used to secure the bone block 26a to the support 14a, for example, then the clamp force can be generated in a direction substantially perpendicular to the path of travel of the support 14a, and in effect, any suitable clamp force could be applied in any direction to the bone block 26a, so long as the bone block 26a is coupled to the support 14a. In addition, it should be noted that the bone engagement member 66a coupled with the proximal end 36 of the support 14a can provide at least three points of contact that can operate to secure the bone block 26a to the support 14a.

With the bone block 26a coupled to the support 14a, and the tendon 26b protected by the tendon support 44a, the support 14a can be advanced to a second position B (FIG. 8) to enable the resection of a first side, a second side and the top surface 26a" of the bone block 26a. The support 14a can be advanced by any suitable technique, such as through a powered or manual application of force to the support 14a, which can operate to move the support 14a linearly with regard to the cutting members 22a to enable the resection of the bone block 26a. In this regard, by employing the two cutting members 22a, as the support 14a moves relative to the cutting members 22, the cutting members 22 can substantially simultaneously resect at least two, but generally, three sides of the bone block 26a to form the cylinder 26c. Thus, the system 10a can form the bone block 26a into the cylinder 26c without requiring any additional cutting operations or repositioning of the bone block 26a.

Once the bone block 26a is resected, the clamp 110 and the stop 104 can be uncoupled from the support 14a to release the cylinder 26c from the support 14a. Then, if applicable, the system 10a can be used to resect a second bone block of the tendon-bone graft 26. Otherwise, the tendon-bone graft 26 can be inserted into a prepared anatomy (not shown).

While specific examples have been described in the specification and illustrated in the drawings, it will be understood by those of ordinary skill in the art that various changes can be made and equivalents can be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this invention, but that the scope of the present disclosure will include any embodiments falling within the foregoing description and the appended claims.

What is claimed is:

1. A system for forming a bone graft comprising:
at least one support that is adapted to support the bone graft;
at least one clamp coupled to the support that is adapted to engage the bone graft to clamp the bone graft to the at least one support;
at least one cutting member that is operable to resect the bone graft, the at least one cutting member having a first dimension greater than a second dimension, the first dimension extending along an axis, with a plurality of teeth positioned incrementally along the axis; and
wherein the at least one cutting member or the at least one support is moveable relative to the other of the at least one cutting member or the at least one support to resect the bone graft.

2. The system of claim 1, wherein the at least one cutting member is movable relative to the at least one support in a direction substantially perpendicular to a clamp force provided by the at least one clamp.

3. The system of claim 1, wherein the at least one support is movable relative to the at least one cutting member in a direction substantially parallel to a clamp force provided by the at least one clamp.

4. The system of claim 1, wherein the at least one support is in a first position and the at least one clamp is in a second position, with the second position opposite the first position such that the bone graft is captured between the at least one support and at the at least one clamp.

5. The system of claim 1, wherein the at least one clamp and the at least one support cooperate to define at least three points of contact on the bone graft.

6. The system of claim 1, wherein the at least one support includes a first side, a second side and a bone engaging surface that is configured to mate with the bone graft.

7. The system of claim 6, further comprising:
a base that includes a guide rail, with the at least one support including a channel formed opposite the bone engaging surface that slidably engages the guide rail to enable the at least one support to move relative to the at least one cutting member.

8. The system of claim 7, wherein the at least one clamp is coupled to a third side of the at least one support in an engaged position to secure the bone graft to the at least one support.

9. The system of claim 1, further comprising a means of protecting the tendon so that the tendon is not damaged during the resection of the bone graft.

10. The system of claim 1, further comprising:
a base, with the at least one support coupled to the base, the at least one support includes a first side, a second side and a bone engaging surface that is configured to mate with the bone graft;
a guide coupled to the base that defines a slot, a first aperture and a second aperture, the first aperture being a mirror image of the second aperture, the first aperture and second aperture receive the at least one cutting member to guide the movement of the at least one cutting member relative to the at least one support; and
wherein the at least one clamp includes a clamp blade and two clamps, the clamp blade slideably received in the slot and including at least one bone engagement member that is adapted to engage the bone graft to clamp the bone graft to the at least one support in an engaged position, and a first one of the clamps is coupled to the first side of the at least one support in the engaged position and a second one of the clamps coupled to the second side of the at least one support in the engaged position to clamp the at least one bone graft to the bone engaging surface.

11. The system of claim 1, further comprising:
a base that includes a guide rail; and
wherein the at least one support includes a first side, a second side, a bone engaging surface that is configured to mate with the bone graft, and a channel formed opposite the bone engaging surface that slidably engages the guide rail to enable the at least one support to move relative to the at least one cutting member.

12. A system for forming a bone graft comprising:
at least one support that is adapted to support the bone graft, the at least one support including a first side, a second side and a bone engaging surface that is configured to mate with the bone graft;
a base, with the at least one support coupled to the base;
a guide coupled to the base that defines a slot;
at least one clamp that is adapted to engage the bone graft to clamp the bone graft to the at least one support, the at least one clamp including a clamp blade slideably received in the slot, the clamp blade including at least one bone engagement member that is adapted to engage the bone graft to clamp the bone graft to the at least one support in an engaged position; and
at least one cutting member that is operable to resect the bone graft,
wherein the at least one cutting member or the at least one support is moveable relative to the other of the at least one cutting member or the at least one support to resect the bone graft.

13. The system of claim 12, wherein the at least one clamp comprises two clamps, with one of the clamps coupled to the first side of the at least one support in the engaged position and a second one of the clamps coupled to the second side of the at least one support in the engaged position to clamp the at least one bone graft to the bone engaging surface.

14. The system of claim 13, wherein the guide defines a first aperture and a second aperture, the first aperture being a mirror image of the second aperture, and the first aperture and second aperture receive the at least one cutting member to guide the movement of the at least one cutting member relative to the at least one support.

15. The system of claim 14, wherein the clamps are in a disengaged position when the at least one cutting member is slideably engaged in the first aperture or the second aperture, and the clamp blade is engaged with the bone graft when the at least one cutting member is slideably engaged in the first aperture or the second aperture.

16. The system of claim 15, wherein the clamps are in the engaged position when the at least one cutting member is slideably engaged in the first aperture and the second aperture, and the clamp blade is disengaged with the bone graft when the at least one cutting member is slideably engaged in the first aperture and the second aperture.

17. The system of claim 12, wherein the guide further comprises a lock that enables the clamp blade to be fixed relative to the guide.

18. A system for forming a bone graft comprising:
at least one support that is adapted to support the bone graft;
at least one clamp that is adapted to engage the bone graft to clamp the bone graft to the at least one support; and
at least one cutting member that is operable to resect the bone graft, the at least one cutting member comprising a plurality of broach teeth, the plurality of broach teeth having a cutting surface, the cutting surface of each of the plurality of broach teeth incrementally decreasing from a proximal broach tooth to a distal broach tooth,
wherein the at least one cutting member or the at least one support is moveable relative to the other of the at least one cutting member or the at least one support to resect the bone graft.

19. The system of claim 18, wherein the at least one cutting member includes a half pipe and the plurality of broach teeth are coupled to the half pipe to enable the resection of a first side of the bone graft.

20. The system of claim 18, wherein the at least one cutting member comprises two half pipes, and the plurality of broach teeth are coupled to each of the half pipes to enable the substantially simultaneous resection of at least a first side and a second side of the bone graft.

* * * * *